United States Patent [19]

Wirt et al.

[11] 4,196,724
[45] Apr. 8, 1980

[54] TONGUE LOCKING DEVICE

[76] Inventors: Winton W. Wirt, Rte. 3, Box 30, Crystal River, Fla. 32629; Desmond C. Prevatt, P.O. Box 284, Yankeetown, Fla. 32698; William H. Frecker, 512 E. Kennedy Blvd., Tampa, Fla. 33602

[21] Appl. No.: 873,936

[22] Filed: Jan. 31, 1978

[51] Int. Cl.² .............................................. A61B 1/24
[52] U.S. Cl. .................................... 128/136; 128/12; 128/299; 433/140
[58] Field of Search .................................. 128/12–16, 128/133, 136, 278, 297–300, 281–282, 208; 32/33

[56] References Cited

U.S. PATENT DOCUMENTS

| 374,122 | 11/1887 | Genese | 128/15 |
| 480,787 | 8/1892 | Scott | 128/16 X |
| 2,482,116 | 9/1949 | Lanahan | 128/15 |
| 2,945,496 | 7/1960 | Fosdal | 128/300 X |
| 3,387,610 | 6/1968 | Richmond | 128/278 |
| 3,557,456 | 1/1971 | Hutchinson | 32/33 |
| 3,946,736 | 3/1976 | Neward | 128/278 |

Primary Examiner—Dalton L. Truluck
Attorney, Agent, or Firm—Clarence A. O'Brien; Harvey B. Jacobson

[57] ABSTRACT

A suction producing formation is elastically contracted to apply suction upon release, to a tongue receiving receptacle inserted into the mouth of a patient. The tongue tip is thereby wedgingly engaged with the rearwardly converging walls of the receptacle to seal a connecting conduit so as to maintain a suction holding pressure on the tongue.

12 Claims, 13 Drawing Figures

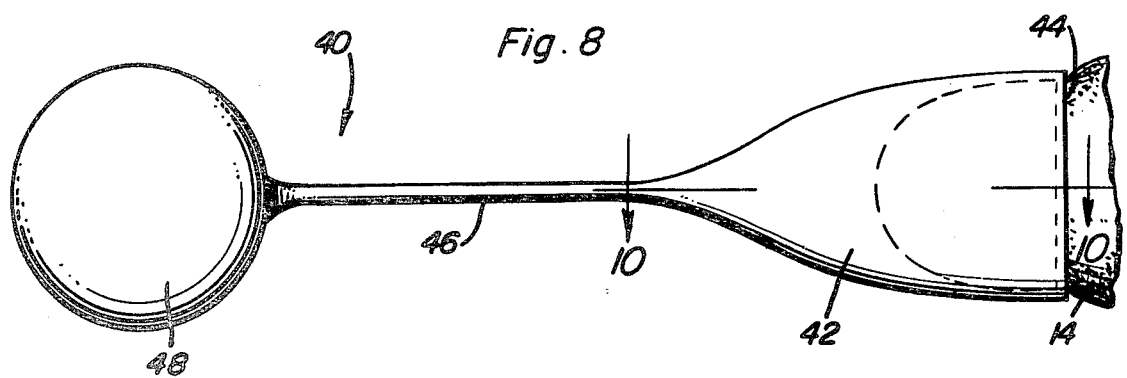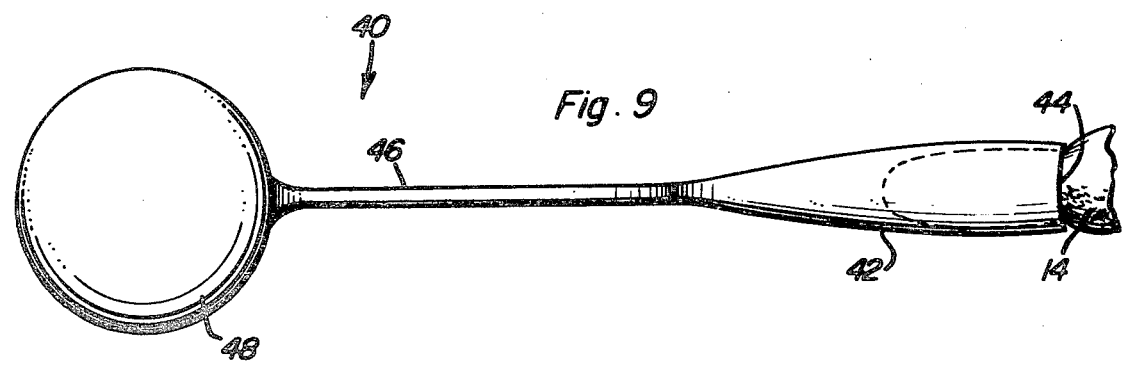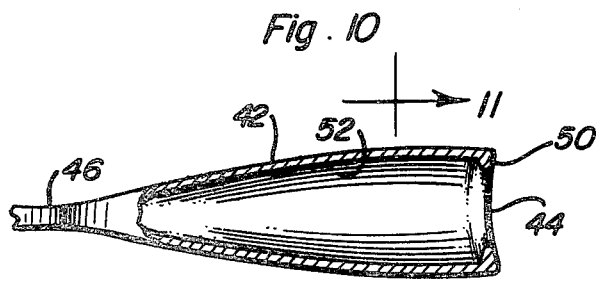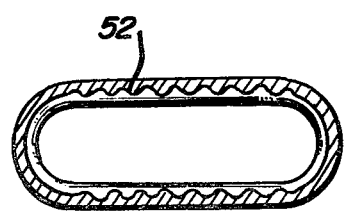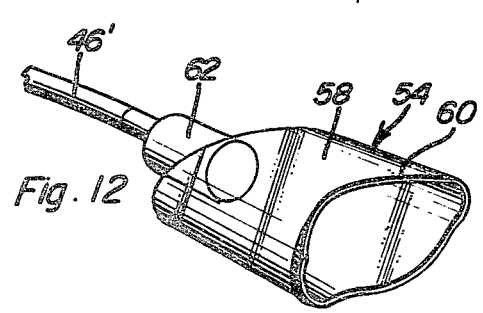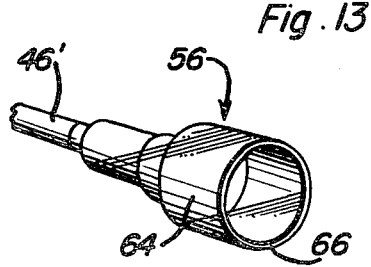

TONGUE LOCKING DEVICE

BACKGROUND OF THE INVENTION

This invention relates to tongue holding devices for patients under the effects of anesthesia, when unconscious, in a coma or when medical or dental work is being done in the mouth or throat and control over the tongue is required by the attending physician.

Tongue engaging devices adapted to be inserted into a patient's mouth are well known, including tongue depressors and clamps. A fluid pressure clamp is shown in U.S. Pat. No. 3,903,894 to Rosen. Bulb operated atomizer and syringe, and suction cup holding devices are also well known.

No prior art known to applicants, suggest the use of suction holding devices adapted to be inserted into the mouth of a patient to immobilize the tongue without holding it against a surface of the oral cavity so as to give the attending physician better outside control of the patient's tongue.

It is therefore an important object of the present invention to provide a tongue holding device which is more easily and quickly applied, disposable so as to lessen the chances of transferring contamination and more compatible for use in the mouth of a patient as compared to devices heretofore available.

SUMMARY OF THE INVENTION

In accordance with the present invention, a rearwardly converging receptacle having a tongue receiving end is dimensioned for insertion into the mouth of a patient to wedgingly receive the tip of the tongue therein in out of contact relation to the surfaces of the oral cavity. The tongue is operative to seal a conduit connecting the receptacle to a suction producing device externally of the mouth in the form of an elastically contractable bulb or bellows formation.

In one form of the invention, a chin engaging element guidingly positions the bellows in front on the patient's mouth while a gas conducting tube is formed integral with the device in another form of the invention for supply of oxygen to the patient. Differently shaped tongue receptacles all having a rearwardly converging configuration are used to suit different patients or requirements.

These, together with other objects and advantages which will become subsequently apparent, reside in the details of construction and operation as more fully hereinafter described and claimed, reference being had to the accompanying drawings forming a part hereof, wherein like numerals refer to like parts throughout.

BRIEF DESCRIPTION OF THE DRAWINGS

FIG. 8 is a top plan view of yet another embodiment of the invention.

FIG. 9 is a side elevational view of the device shown in FIG. 8.

FIG. 10 is an enlarged partial sectional view taken through a plane indicated by section line 10—10 in FIG. 8.

FIG. 11 is a transverse sectional view taken through a plane indicated by section line 11—11 in FIG. 10.

FIG. 12 is a perspective view of a modified form of tongue receiving receptacle associated with another form of the invention.

FIG. 13 is a perspective view of yet another form of tongue receiving receptacle.

DETAILED DESCRIPTION OF PREFERRED EMBODIMENTS

Figure 1:
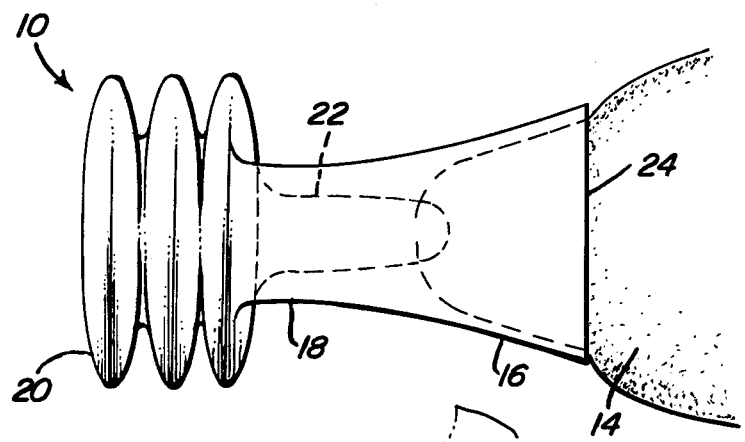
FIG. 1 is a top plan view of one form of the invention.
Figure 2:
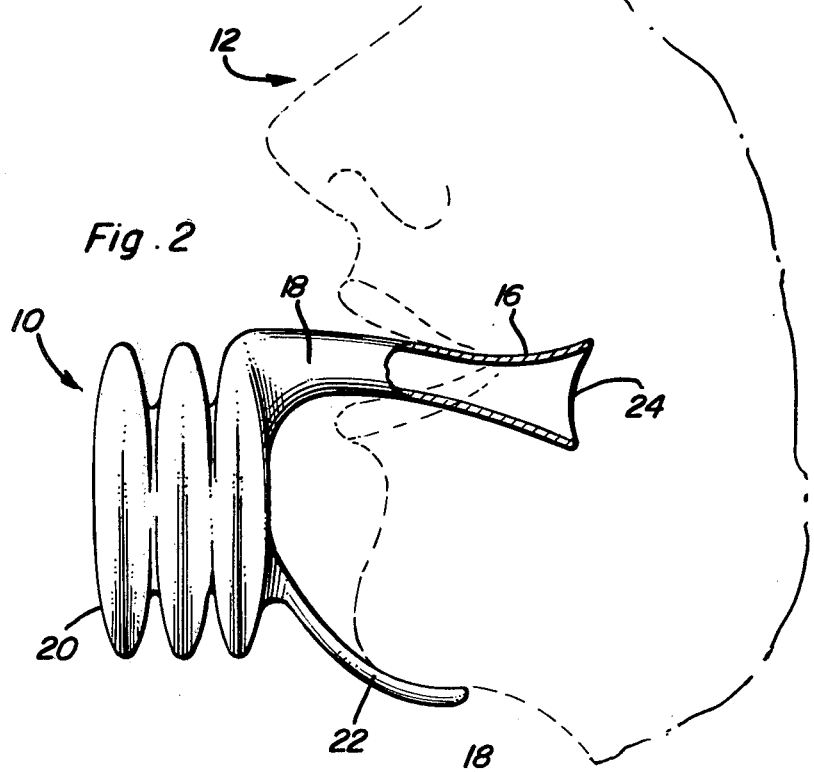
FIG. 2 is a side elevational view of the device shown in FIG. 1, with a portion broken away and shown in section.
Figure 3:
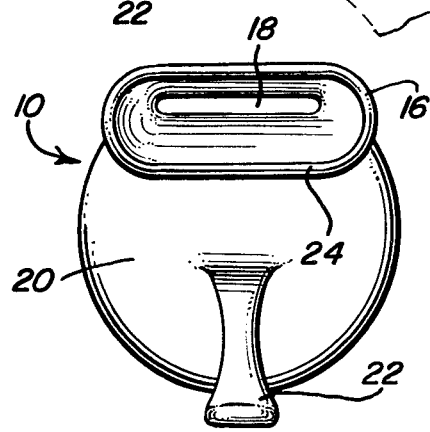
FIG. 3 is a front elevational view of the device shown in FIG. 1.

Referring now to the drawings in detail, FIGS. 1, 2 and 3 illustrate one form of a tongue holding device generally referred to by reference numeral 10. As best shown in FIG. 2, the device 10 is adapted to be inserted into the mouth of a patient 12 to engage and prevent swallowing of the tongue 14. In this form of the invention, the device 10 includes a receptacle portion 16 interconnected by a conduit portion 18 to a flexible bellows formation 20 constituting an elastically contractable handle grip. The entire device 10 may be integrally formed from a blow molded, polyethylene plastic and includes an arcuate chin engaging element 22.

The receptacle portion 16 is laterally elongated in cross-sectional shape and converges rearwardly from a tongue receiving end 24 so as to wedgingly receive the tip of tongue 14 therein as best seen in FIG. 1. The tongue will accordingly seal the passage in conduit portion 18 communicating with the space enclosed by the bellows 20 which is volumetrically larger than the space enclosed by the receptacle portion in the expanded condition of the bellows as shown.

The bellows formation 20 is elastically contractable in a direction generally parallel to the conduit portion 18 extending forwardly therefrom. Further, the bellows formation extends laterally from the conduit portion to enable it to be grasped in the hand of an operator and squeezed in order to cause contraction of its enclosed volume. With the bellows formation held contracted in the hand, the receptacle portion 16 may be inserted into the mouth for reception of the tongue therein. The chin engaging element 22 will guide proper positioning of the device 10 for this purpose. Once the tongue is received in the receptacle portion, the bellows formation is released to produce a suction pressure therein communicated to the receptacle portion through the conduit portion. The tongue is thereby drawn into the receptacle portion and wedgingly seals the conduit portion to maintain a suction pressure therein to lock it onto the tongue. Withdrawal of the tongue is accordingly prevented.

Figure 4:
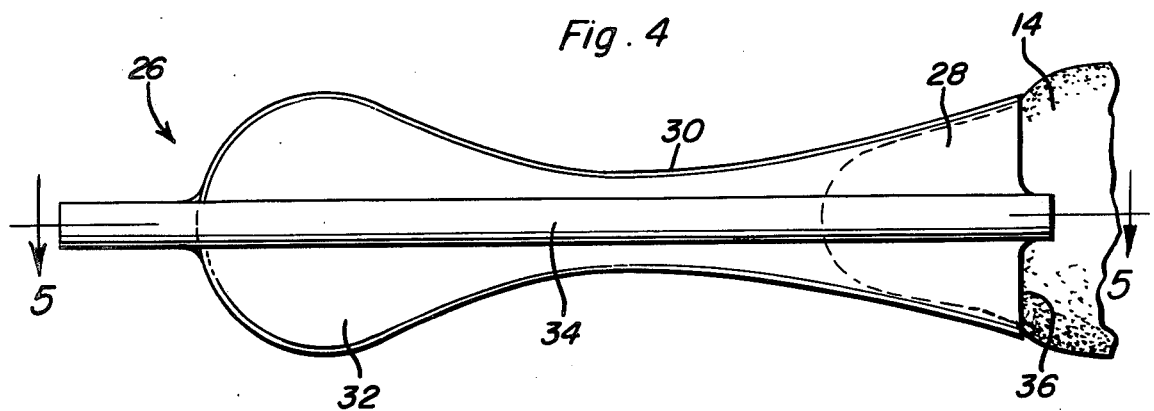
FIG. 4 is a top plan view of another form of the invention.
Figure 5:
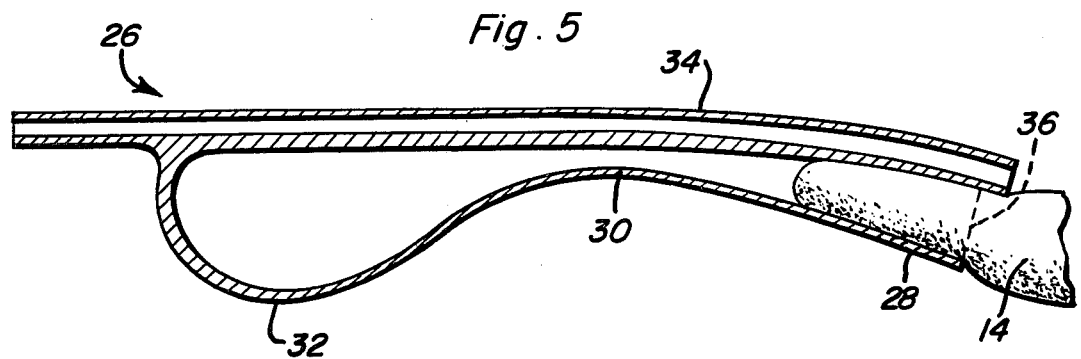
FIG. 5 is a side sectional view taken through a plan indicated by section line 5—5 in FIG. 4.

FIGS. 4 and 5 illustrate another form of tongue holding device 26 serving the same function as device 10 and also provided with a rearwardly converging receptacle portion 28 connected by a conduit portion 30 to an elastically contractable handle grip in the form of a bulb formation 32. The bulb formation 32 also extends laterally from the conduit portion and encloses a larger volume than the receptacle portion in the expanded condition shown. The bulb formation is however contracted in a direction transverse to the conduit passage to expel the air in preparation for the application of suction pressure to the tongue 14 upon release. Use and operation of the device 26 is similar to that of device 10 except that the device 26 also has an elongated gas conducting tube 34 formed integral therewith. The tube 34 is positioned along the top of the bulb formation 32, the conduit portion 30 and receptacle portion 28 and extends beyond the tongue receiving end 36 so as to deliver a gas such as oxygen to the patient while the tongue is being held.

Figure 6:
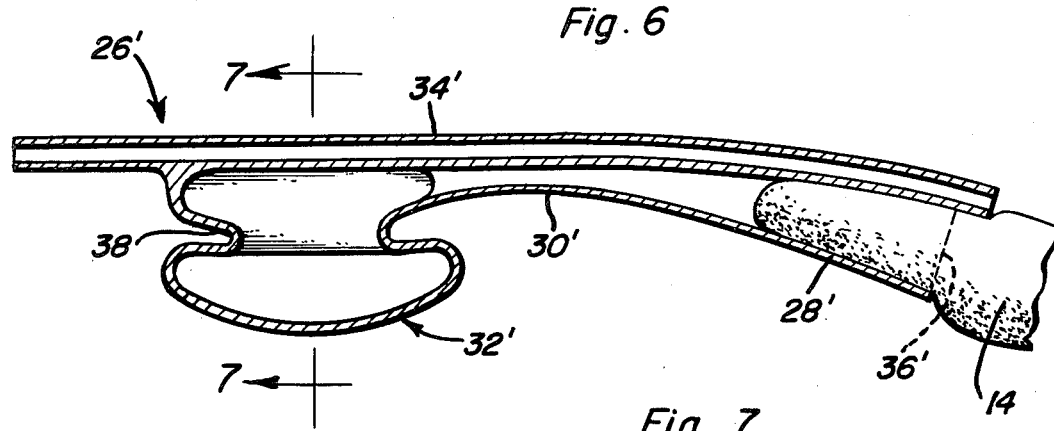
FIG. 6 is a side sectional view similar to FIG. 5 showing a modification thereof.
Figure 7:
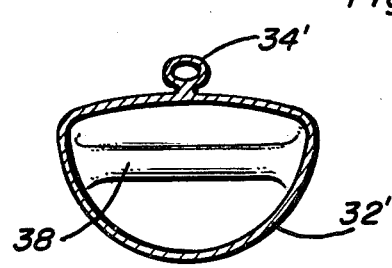
FIG. 7 is a transverse sectional view taken through a plane indicated by section line 7—7 in FIG. 6.

FIGS. 6 and 7 illustrate a device 26' which is the same in construction and use as the device 26 except for the contractable formation 32'. The formation 32' is provided with an intermediate fold 38 so as to form a bellows type of suction producing means deformable in a direction transverse to the conduit portion 30' when grasped in the hand prior to reception of the tongue within receptacle portion 28'. A tube 34' also extends beyond the tongue receiving end 36'.

In FIGS. 8 and 9, a tongue holding device 40 is shown having a tongue receiving receptacle 42 converging rearwardly from front end 44 to a circular cross-sectional conduit 46 connecting the receptacle to a generally spherical suction producing bulb 48. The device 40 is utilized in a manner hereinbefore described with respect to device 10. As shown in FIGS. 10 and 11, the receptacle 42 is formed with inwardly projecting lips 50 at the tongue receiving end 44 and is provided with tongue gripping ribs 52 to enhance the holding action.

The device 40 shown in FIGS. 8-11 may be cheaply made of an integral, disposable material. Alternatively, the device may be made of a more durable material except for the tongue receiving receptacle separable from the conduit 46' as shown in FIGS. 12 and 13, respectively illustrating receptacles 54 and 56. The receptacle 54 shown in FIG. 12 is oval-shaped in cross-section along a larger diameter portion 58 on which a recessed tongue receiving edge 50 is formed. A smaller diameter portion 62 of the receptacle 54 is connected to the conduit 46'. The larger diameter portion 64 of the receptacle 56 is circular in cross-section at the tongue receiving end 66 while the smaller diameter portion 68 is adapted to be connected to the conduit 46'. Both receptacles 54 and 56 thus converge rearwardly from the tongue receiving ends by virtue of a stepped diameter construction. The tongue will be received in the large diameter portion and seal the small diameter portion through which suction pressure is applied.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention.

What is claimed as new is as follows:

1. A device for holding the tip of a tongue of a person in out of contact relation to the mouth surfaces, comprising an elongated receptacle having an open tongue receiving means on one end insertable into the mouth of the person having a cross-sectional configuration converging rearwardly from said tongue tip receiving end, an elastically contractable handle grip means having an expanded condition in which a larger volume is enclosed therein relative to the volume enclosed by the receptacle, a conduit connecting the handle grip means to the receptacle for applying suction pressure in response to release of the handle grip means from a contracted condition, the suction pressure being operative to draw the tongue tip longitudinally into said tongue tip receiving means of the receptacle for wedging engagement therewith to substantially seal the conduit and thereby prevent withdrawal of the tongue from the receptacle.

2. The combination of claim 1 wherein said contractable handle grip means is a flexible bellows projecting laterally from the conduit to which it is connected.

3. The combination of claim 2 wherein said cross-section of the receptacle is laterally elongated.

4. The combination of claim 1 wherein said cross-section of the receptacle is laterally elongated.

5. The combination of claim 4 wherein said receptacle is provided within internal gripping ribs.

6. The combination of claim 2 including a chin engaging element projecting from the contractable handle grip means in spaced relation to the conduit.

7. The combination of claim 1 including a gas conducting tube fixed to the handle grip means, the conduit and the receptacle, said tube extending beyond the tongue receiving end.

8. The combination of claim 1 wherein said contractable handle grip means is a manual squeeze bulb means.

9. The combination of claim 1 including a chin engaging element projecting from the contractable handle grip means in spaced relation to the conduit.

10. The combination of claim 1 wherein the receptacle is oval-shaped in cross-section.

11. The combination of claim 1 wherein the receptacle includes a diametrically large portion and a diametrically smaller portion to which the conduit is connected.

12. The combination of claim 11 wherein said diametrically large portion is oval-shaped in cross-section.

* * * * *